(12) United States Patent
Ikeda et al.

(10) Patent No.: US 9,616,369 B2
(45) Date of Patent: Apr. 11, 2017

(54) INERTIAL FILTER

(75) Inventors: Takuji Ikeda, Yamatokohriyama (JP);
Yoshio Otani, Kanazawa (JP); Masami Furuuchi, Kanazawa (JP); Takafumi Seto, Kanazawa (JP)

(73) Assignee: NITTA CORPORATION, Osaka (JP)

( * ) Notice: Subject to any disclaimer, the term of this patent is extended or adjusted under 35 U.S.C. 154(b) by 82 days.

(21) Appl. No.: 14/127,068

(22) PCT Filed: Aug. 8, 2011

(86) PCT No.: PCT/JP2011/004490
§ 371 (c)(1),
(2), (4) Date: Dec. 17, 2013

(87) PCT Pub. No.: WO2012/176245
PCT Pub. Date: Dec. 27, 2012

(65) Prior Publication Data
US 2014/0137523 A1    May 22, 2014

(30) Foreign Application Priority Data
Jun. 20, 2011  (JP) .................................. 2011-136696

(51) Int. Cl.
*B01D 51/00* (2006.01)
*B01D 46/00* (2006.01)
(Continued)

(52) U.S. Cl.
CPC ......... *B01D 46/0023* (2013.01); *B01D 45/04* (2013.01); *B01D 45/08* (2013.01);
(Continued)

(58) Field of Classification Search
CPC ............ B01D 46/0002; B01D 46/2411; B01D 46/521; B01D 46/0005; B01D 46/10;
(Continued)

(56) References Cited

U.S. PATENT DOCUMENTS

| 4,274,846 A * | 6/1981 | Smith ....................... 73/863.22 |
| 2002/0069709 A1* | 6/2002 | Roberts et al. ............ 73/863.23 |

(Continued)

FOREIGN PATENT DOCUMENTS

| CA | 2 803 088 | 1/2012 |
| JP | 49-3689 | 1/1974 |

(Continued)

*Primary Examiner* — Dung H Bui
(74) *Attorney, Agent, or Firm* — Norris McLaughlin & Marcus, P.A.

(57) ABSTRACT

An inertial filter to be disposed in the air flow path of a stream of air containing nanoparticles includes plural particle classifying sheets having plural mesh-like holes are disposed in the air flow path. The plural particle classifying sheets are stacked on each other in a manner that a part of at least one of the particle classifying sheets overlaps with the other particle classifying sheet. The inertial filter can adjust a classification diameter by adjusting a shadow area ratio on a projection view obtained by virtually projecting the plural particle classifying sheets from a downstream side to an upstream side of the air flow path.

3 Claims, 11 Drawing Sheets (51) Int. Cl.
*B01D 46/24* (2006.01)
*B01D 46/52* (2006.01)
*B01D 46/10* (2006.01)
*B01D 45/08* (2006.01)
*B01D 45/04* (2006.01)
*G01N 1/22* (2006.01)
*B01D 46/12* (2006.01)
*G01N 15/02* (2006.01)

(52) U.S. Cl.
CPC ..... *B01D 46/0002* (2013.01); *B01D 46/0005* (2013.01); *B01D 46/0041* (2013.01); *B01D 46/10* (2013.01); *B01D 46/12* (2013.01); *B01D 46/2411* (2013.01); *B01D 46/521* (2013.01); *G01N 1/2208* (2013.01); *G01N 1/2211* (2013.01); *G01N 15/0272* (2013.01); *G01N 15/0255* (2013.01)

(58) Field of Classification Search
CPC .... B01D 45/04; B01D 45/08; G01N 15/0255; G01N 15/0272
USPC ......... 55/418, 525, 526, 489, 495; 73/28.04, 73/28.05, 28.06, 863.22, 863.23
See application file for complete search history.

(56) References Cited

U.S. PATENT DOCUMENTS

| | | |
|---|---|---|
| 2005/0205483 A1 | 9/2005 | Birmingham et al. |
| 2006/0081515 A1 | 4/2006 | Gorbunov et al. |
| 2007/0056390 A1 | 3/2007 | Harley |
| 2013/0086876 A1 | 4/2013 | Ikeda |

FOREIGN PATENT DOCUMENTS

| | | |
|---|---|---|
| JP | 61-135583 | 8/1986 |
| JP | 61-291014 | 12/1986 |
| JP | 10-314676 | 12/1998 |
| JP | 2001-104736 | 4/2001 |
| JP | 2006-198577 | 8/2006 |
| JP | 2006-263713 | 10/2006 |
| JP | 2008-70222 | 3/2008 |
| JP | 2009-115362 | 5/2009 |
| JP | 2011-12977 | 1/2011 |
| JP | 4714915 | 7/2011 |
| SU | 840707 | 6/1981 |
| WO | WO-2004/003520 | 1/2004 |

* cited by examiner

PRIOR ART

INERTIAL FILTER

BACKGROUND OF THE INVENTION

The invention relates to inertial filters to be disposed in an air flow path that are configured to classify submicron or smaller particles contained in a stream of air flowing in the air flow path, particularly nanoparticles having particle sizes equal to or smaller than 100 nm, by utilizing the effect of inertial impaction.

Figure 11:
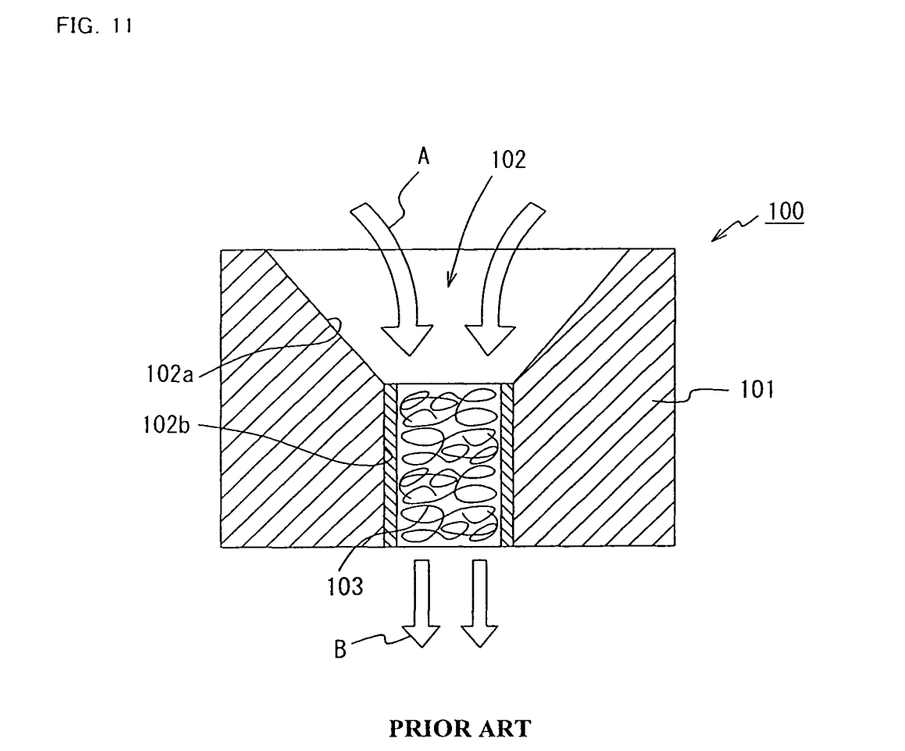

A conventional inertial filter 100 is described below referring to FIG. 11. The conventional inertial filter 100 is disposed in an air flow path to classify particles. The conventional filter 100 has a cylindrical filter body 101, and the filter body 101 has a through cavity 102 having a circular shape in cross section and penetrating through from the upstream side to the downstream side of an airstream passage. The through cavity 102 includes a diametrically-reduced through cavity 102a and a diametrically-constant through cavity 102b. The diametrically-reduced through cavity 102a is provided on the upstream side of the airstream passage and has an inner diameter progressively smaller. The diametrically-constant through cavity 102b is continuous to the diametrically-reduced through cavity 102a on the downstream side of the airstream passage and has an inner diameter dimensionally fixed. The diametrically-constant through cavity 102b is filled with a metal fiber 103 which is an example of incompressible fibers. The metal fiber 103 is secured by a mechanism not illustrated in the drawing so that the metal fiber 103 does not fall off from the diametrically-constant through cavity 102b and drop downward in an airstream passing direction.

In the inertial filter 100, its internal pressure is lowered to or under an external pressure by a suctioning force of a pump not illustrated in the drawing, so that a stream of air is generated in the through cavity 102 by a pressure difference between the internal and external pressures in a direction from an arrow A toward an arrow B illustrated in the drawing to allow for classification of particles. The pressure difference is generated by lowering the internal pressure from the external pressure. The stream of air increases its flow velocity in the diametrically-reduced through cavity 102a, and the flow velocity becomes constant once the stream of air enters the diametrically-constant through cavity 102b. Then, fine particles contained in the stream of air is collided with and captured (collected) by the metal fiber 103 in the diametrically-constant through cavity 102b.

Background prior art includes JP Patent Application Publication No. 2008-70222.

SUMMARY OF THE INVENTION

The conventional inertial filter 100 has the technical problems described below.
  Problem 1: difficulty in achieving aimed initial classifying characteristics because of the lack of uniformity in the spatial density distribution, orientation, and shape of the fiber,
  Problem 2: difficulty in filling the diametrically-constant through cavity 102b with the metal fiber 103 at an equal density, and random density of the metal fiber 103 filling the diametrically-constant through cavity 102b makes the classifying characteristics easily variable, undermining the stability of the particle classifying operation,
  Problem 3: compression of the metal fiber 103 in the airstream passing direction due to pressure applied by the stream of air during the particle classification adversely affects the classifying characteristics, undermining the stability of the particle classifying operation, and
  Problem 4: possible changes in the spatial density of the metal fiber 103 in the diametrically-constant through cavity 102b during wash of the inertial filter are difficult to quantify, often compromising reuse of the inertial filter.
  Problem 5: difficulty in simple and quick adjustment of a classifying performance.

Faced with these technical problems, the invention provides an inertial filter having an ability to easily adjust its classifying performance, wherein all of these technical problems are solved.

An inertial filter according to the invention is an inertial filter to be disposed in an air flow path for a stream of air containing nanoparticles to pass through, the inertial filter being configured to collect the nanoparticles in the air flow path by utilizing an effect of particle inertia, the inertial filter collecting the nanoparticles having smaller particle sizes as a flow velocity of the stream of air is higher, wherein
  a plurality of particle classifying sheets are disposed on the air flow path, the plurality of particle classifying sheets having a plurality of holes formed in a mesh-like pattern,
  the plurality of particle classifying sheets are stacked on each other in a manner that a part of at least one of the plurality of particle classifying sheets overlaps with the other particle classifying sheet, and
  a classification diameter can be adjusted by adjusting a shadow area ratio on a projection view obtained by virtually projecting the plurality of particle classifying sheets from a downstream side to an upstream side of the air flow path.

Preferably, the inertial filter includes a flow rate adjusting nozzle located further on the upstream side of the air flow path than the particle classifying sheets and having a through cavity diametrically reduced in an airstream passing direction. The flow rate adjusting nozzle is replaceable with another flow rate adjusting nozzle having a different number of through cavities or having a through cavity diametrically reduced by a different diameter reducing ratio to allow for adjustment of the flow velocity. The plurality of particle classifying sheets are stacked on each other in a manner that the plurality of particle classifying sheets seal a whole surface of a downstream-side opening of the through cavity of the flow rate adjusting nozzle.

Preferably, the plurality of particle classifying sheets are stacked on each other with a spacer interposed therebetween.

The fluid to be filtered is not necessarily limited to gaseous matters and may be liquids or matters in other forms.

The particles captured or collected by the inertial filter are not necessarily limited to particles floating in gaseous matters. The particles may be particles floating in solvents, other liquids, or matters in other forms. The types of particles to be classified are not particularly limited, and examples thereof are resinous fine particles, inorganic fine particles, metallic fine particles, and ceramic fine particles. The particles may have any arbitrary shapes.

According to the invention, the classifying performance can be easily adjusted by adjusting the shadow area ratio on the projection view obtained by virtually projecting the plurality of particle classifying sheets from the downstream side to the upstream side of the air flow path.

According to the invention, the flow rate adjusting nozzle having the through cavity diametrically smaller in the airstream passing direction is located further on the upstream side of the air flow path than the particle classifying sheets, and the flow rate adjusting nozzle is replaceable with another flow rate adjusting nozzle having a different number of through cavities or having a through cavity diametrically reduced by a different diameter reducing ratio to allow for adjustment of the flow velocity. Further, the plurality of particle classifying sheets seal the whole surface of the downstream-side opening of the through cavity of the flow rate adjusting nozzle. The inertial filter according to the invention thus characterized is excellent in initial classifying characteristics and capable of classifying particles in a stable manner over a long period of time.

Figure 1:
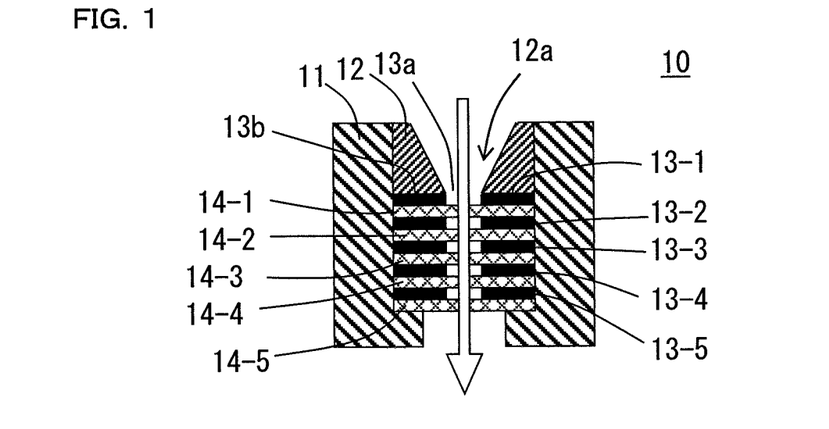
FIG. 1 is a sectional view of an inertial filter according to an embodiment of the invention.
Figure 2:
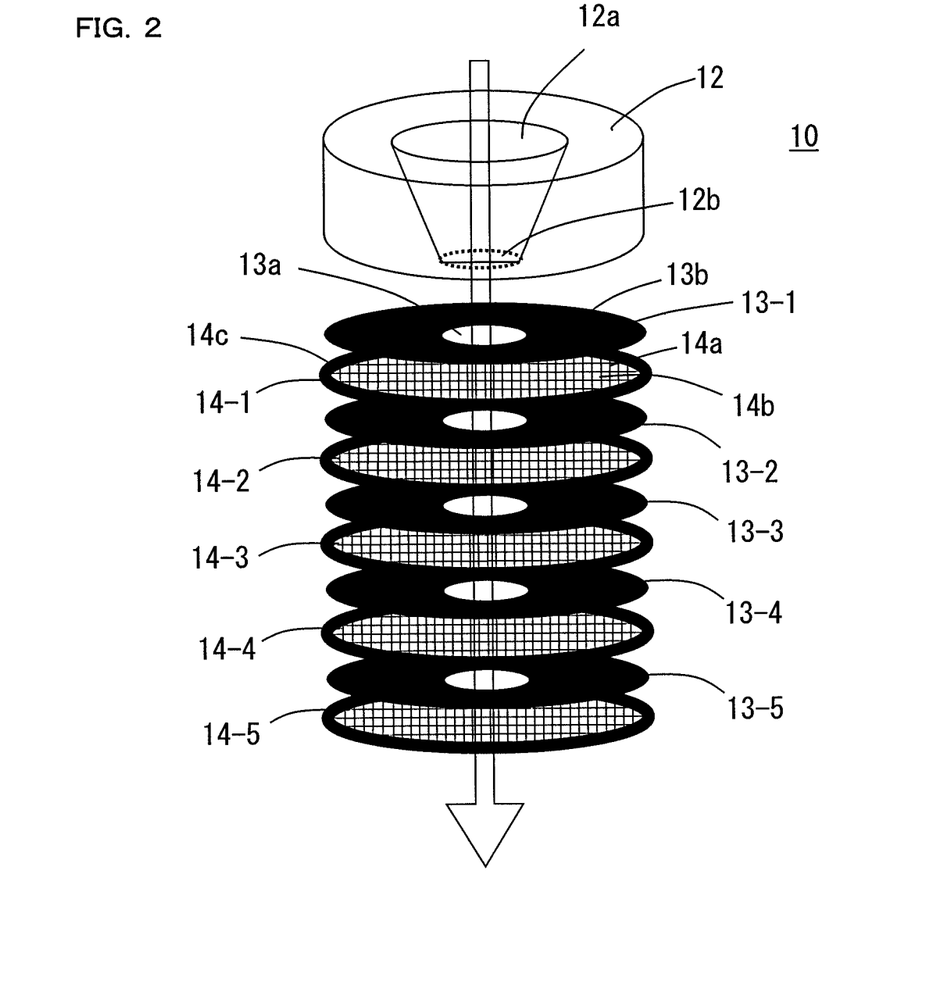
FIG. 2 is an enlarged exploded view of the inertial filter illustrated in FIG. 1.

FIG. 3A is a drawing (1) illustrating shadowed and unshadowed parts on a projection view obtained by projecting a plurality of particle classifying sheets.

FIG. 3B is a drawing (2) illustrating shadowed and unshadowed parts on a projection view obtained by projecting the plurality of particle classifying sheets.

FIG. 4 is a drawing illustrating levels of collection efficiency with different particle sizes and different shadow area ratios.

FIG. 5 is a graph illustrating a relationship between a shadow area ratio ("area ratio of mesh-patterned projection" in the drawing) and a highest level of collection efficiency.

FIG. 6 is a drawing illustrating planar shapes of two particle classifying sheets having mesh-like holes formed in different shapes and a planar shape of the particle classifying sheets when stacked on each other.

FIG. 7 is a conceptual view illustrated to describe a particle collection mechanism of a conventional fiber-layered filter.

FIG. 8 is a conceptual view of particle classification of an inertial filter.

FIG. 9 is a drawing illustrating a relationship between particle sizes and levels of collection efficiency at different filtering speeds in the inertial filter.

FIG. 10 is a drawing illustrating particles accumulated on a mesh-like filtering surface of the inertial filter.

FIG. 11 is a sectional view of a conventional inertial filter.

DETAILED DESCRIPTION OF THE INVENTION

The inertial filter filed by the Applicant of this application, JP Patent No. 4714915, solved a part of the conventional problems described earlier. In this description, this inertial filter is called a basic filter. The basic filter can easily achieve an aimed initial classifying performance and maintain a level of collection efficiency over a long period of time, thereby performing a stable particle classifying operation.

The basic filter has a flow rate adjusting nozzle and particle classifying sheets. The flow rate adjusting nozzle has a diametrically-reduced through cavity having an inner diameter progressively smaller in an airstream passing direction. The flow rate adjusting nozzle adjusts a flow velocity by taking advantage of the structure of the through cavity and thereby changes a classification diameter. The particle classifying sheets are located further on the downstream side of an airstream passage than the flow rate adjusting nozzle. The particle classifying sheet has a plurality of classification holes arranged uniformly in a mesh-like pattern to collect floating fine particles by utilizing an effect of particle inertia. The particle classifying sheet has an area larger than that of a downstream-side opening of the through cavity formed in the flow rate adjusting nozzle. The particle classifying sheet having such a dimension is provided in a manner that covers the whole surface of the downstream-side opening.

After the invention relating to such a basic filter was filed, the Applicant of this application found out; the basic filter having plural particle classifying sheets can deliver a better classifying performance through improvements in the arrangement of the particle classifying sheets in the airstream passing direction than having just one particle classifying sheet. Based on the finding, the invention of this application succeeded in further improving the basic filter.

An inertial filter according to an embodiment of the invention is hereinafter described referring to the accompanied drawings. The structural characteristics of the inertial filter are described referring to FIGS. 1 and 2. FIG. 1 is a sectional view of the inertial, filter according to the embodiment FIG. 2 is an enlarged exploded view of the inertial filter illustrated in FIG. 1.

This inertial filter 10 has a filter support 11, a flow rate adjusting nozzle 12, a plurality of spacers 13-1 to 13-5, and a plurality of particle classifying sheets 14-1 to 14-5. The filter support 11 has a circular inner peripheral surface and a cylindrical shape with opening ends on both sides thereof.

The flow rate adjust my nozzle 12 has a cylindrical shape with opening ends on both sides thereof. An outer peripheral surface of the flow rate adjusting nozzle 12 is located on the upstream side of the airstream passage along the inner peripheral surface of the filter support 11. On an inner peripheral surface of the flow rate adjusting nozzle 12 is provided a through cavity 12*a* diametrically reduced in the airstream passing direction. The flow rate adjusting nozzle 12 is replaceable with another flow rate adjusting nozzle having a diametrically-reduced through cavity 12*a* diametrically reduced by a different diameter reducing ratio to allow for adjustment of the flow velocity. The drawing shows just one through cavity 12*a*. The flow rate adjusting nozzle 12 may have a plurality of through cavities (though not illustrated in the drawing) and be replaceable with another flow rate adjusting nozzle having a different number of through cavities to allow for adjustment of the flow velocity.

The spacers 13-1 to 13-5 have a circular shape in planar view and a small thickness. Each of the spacers 13-1 to 13-5 has an outer diameter substantially equal to the outer diameter of the flow rate adjusting nozzle 12. Further, each of the spacers 13-1 to 13-5 includes a circular opening 13*a* formed at its center and a spacer portion 13*b* around the circular opening 13*a*. These spacers are provided along a direction illustrated with an arrow. In the spacers 13-1 to 13-5, diameters of the openings 13*a* are substantially equal to the diameter of an opening 12*b* formed in the through cavity 12*a* of the flow rate adjusting nozzle 12 on the downstream side in the airstream passing direction. The spacer 13-1 is an uppermost spacer located on the upstream side in the airstream passing direction. In the spacer portion 13*b* of the spacer 13-1, an upper surface is directly in contact with a lower surface of the flow rate adjusting nozzle 12. In the spacers 13-1 to 13-5, outer diameters of the spacer portions 13*b* are substantially equal to the inner diameter of the filter support 11.

The particle classifying sheets 14-1 to 14-5 have a circular shape in planar view and a small thickness. The particle classifying sheets 14-1 to 14-5 each has an outer diameter substantially equal to the outer diameter of the flow rate adjusting nozzle 12. The particle classifying sheets 14-1 to 14-5 each includes a plurality of mesh-like holes 14a, mesh portions 14b that define the mesh-like holes 14a, and a peripheral portion 14c that supports the mesh portions 14b.

In the particle classifying sheets 14-1 to 14-5, outer diameters of the peripheral portions 14c are substantially equal to the outer diameters of the spacer portions 13b in the spacers 13-1 to 13-5. The particle classifying sheets 14-1 to 14-5 are stacked on one another in the airstream passing direction with the spacers 13-1 to 13-5 alternately interposed therebetween. The particle classifying sheets 14-1 to 14-5 have an equal shape, and the mesh-like holes 14a of these sheets all have a square shape. The shape of the mesh-like hole is not particularly limited thereto and may be other shapes such as polygonal shapes.

In the downstream-side opening 12b of the through cavity 12a provided in the flow rate adjusting nozzle 12, a multi-layered structure is provided, in which the spacers 13-1 to 13-5 the particle classifying sheets 14-1 to 14-5 are alternately stacked, and the whole surface of the downstream-side opening 12b of the through cavity 12a provided in the flow rate adjusting nozzle 12 is sealed with the multilayered structure.

Virtually projecting the multilayered structure, in which the spacers 13-1 to 13-5 and the particle classifying sheets 14-1 to 14-5 are alternately stacked, from the downstream side to the upstream side of the air flow path, a projection view with shadowed and unshadowed parts is projected on a virtual plane facing the downstream-side opening 12b of the flow rate adjusting nozzle 12. The shadowed parts are projected on the projection view because light is blocked in these parts by the mesh portions 14b and the peripheral portions 14c of the particle classifying sheets 14-1 to 14-5.

Virtually projecting the multilayered structure, in which the spacers 13-1 to 13-5 and the particle classifying sheets 14-1 to 14-5 are alternately stacked, from the downstream side to the upstream side of the air flow path, an area ratio of the shadowed warts can be adjusted on the projection view projected on the virtual plane facing the downstream-side opening 12b. According to the invention, therefore, the classification diameter and the collecting efficiency of the inertial filter can be effectively adjusted by adjusting the area ratio on the projection view.

Figure 3A:
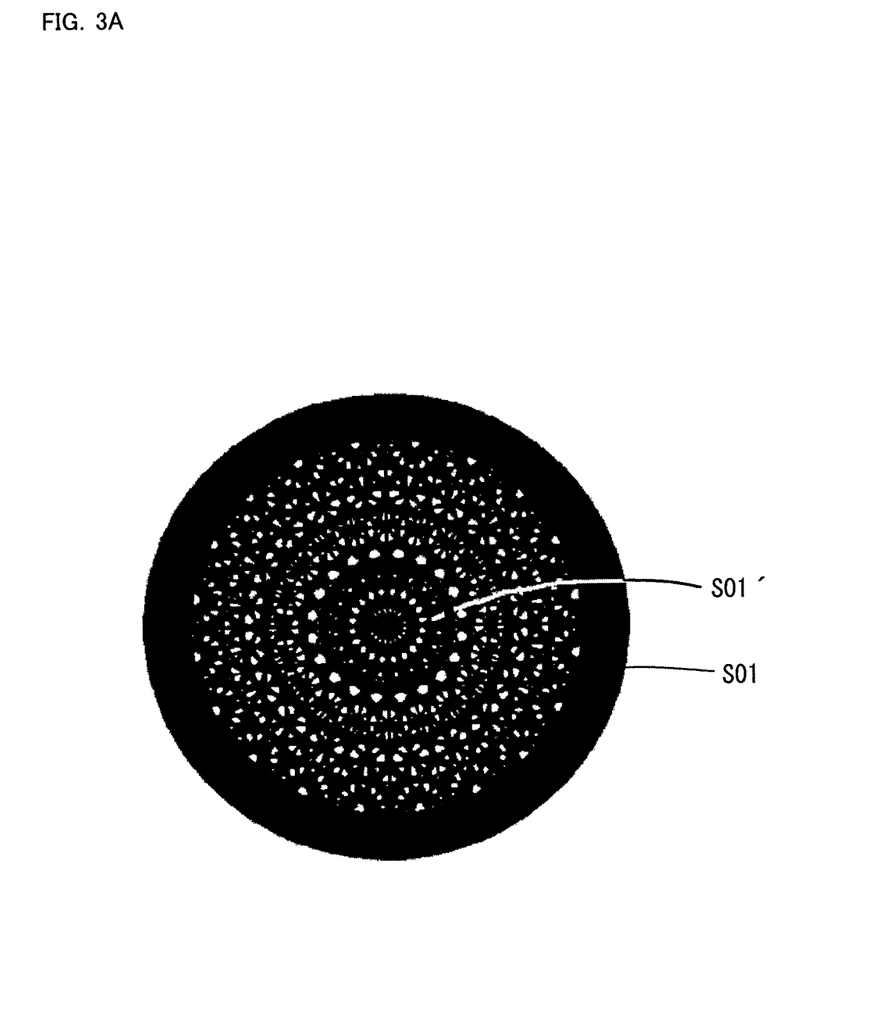
Figure 3B:
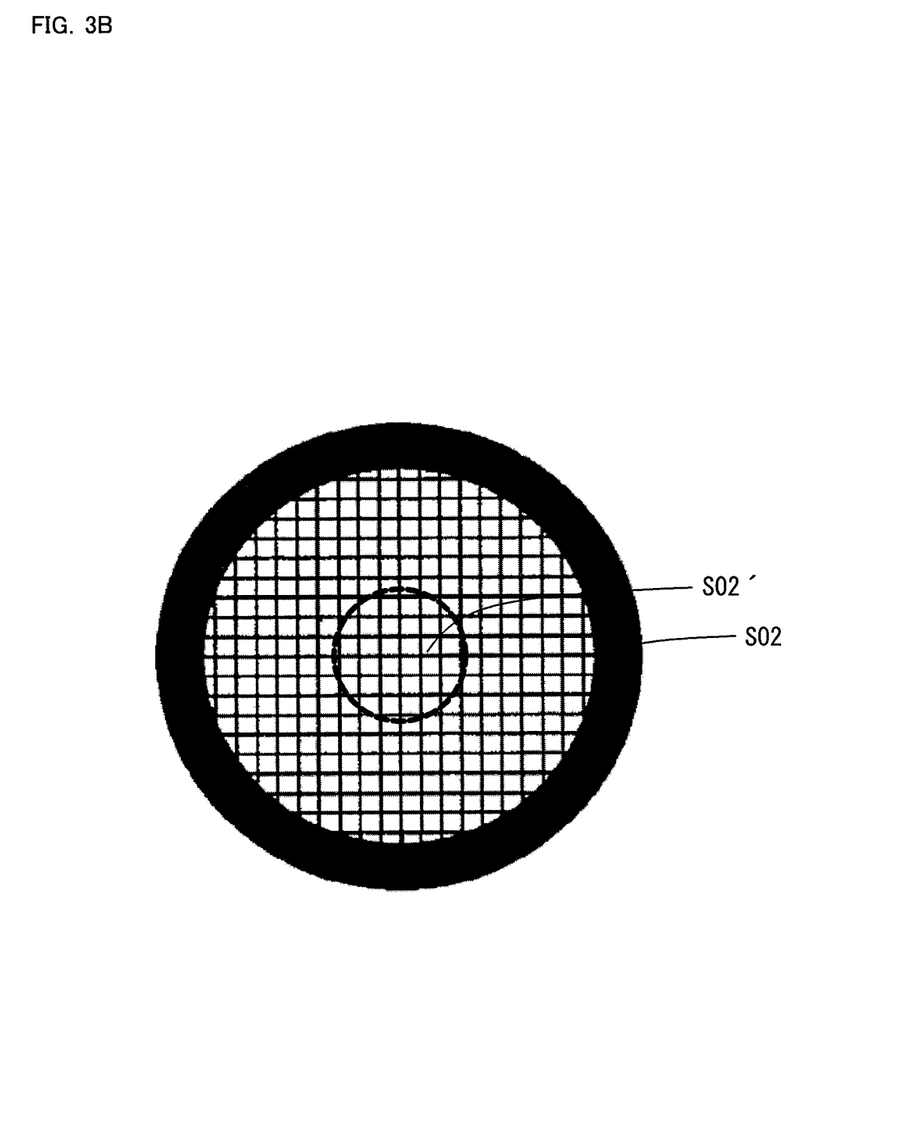
Figure 4:
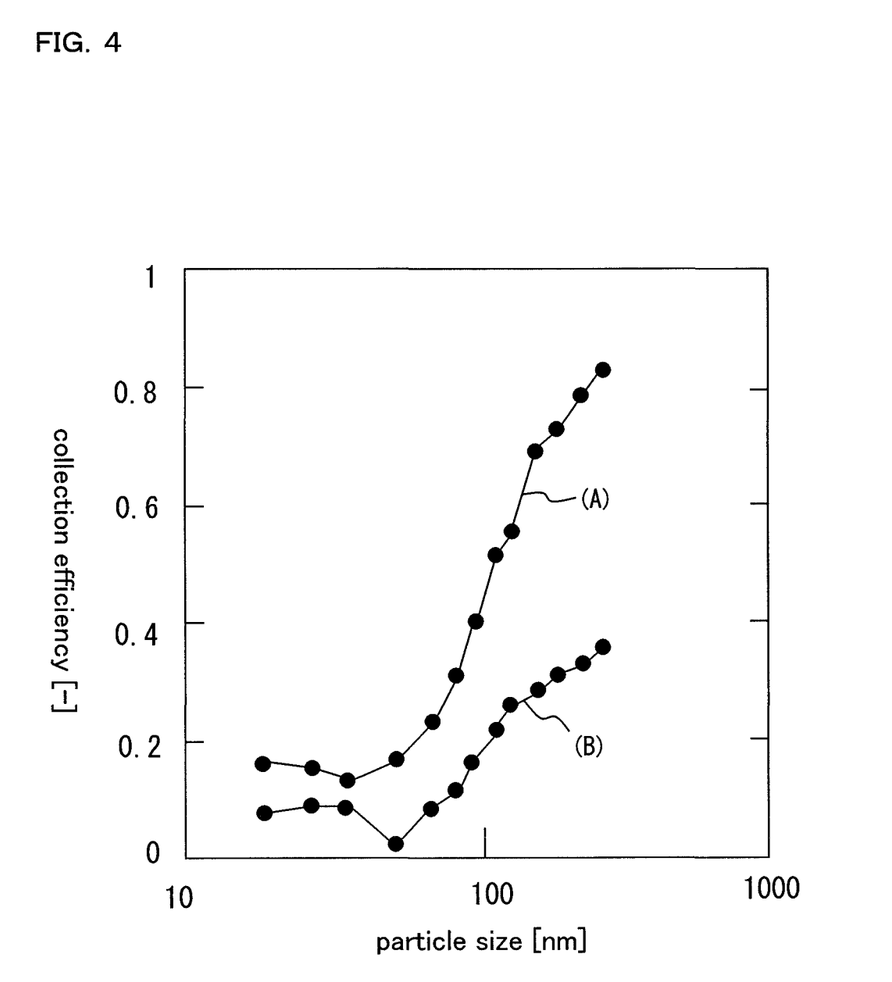

Referring to FIGS. 3A, 3B, and 4 are described in detail the adjustments of the classification diameter and the collection efficiency of the inertial filter by using the particle classifying sheets 14-1 to 14-5. FIGS. 3A and 3B illustrate shadowed parts S01 and S02 (black parts in the drawings) on the projection view where light is blocked by the respective mesh portions 14b and the peripheral portions 14c supporting the mesh portions 14b of the particle classifying sheets 14-1 to 14-5 (hereinafter, referred to as projected parts S01 and S02). In the illustrations of FIGS. 3A and 3B, the projected parts S01 and S02 respectively include shadowed parts S01' and S02' (black parts in the drawings) in a range marked with a broken line that faces the downstream-side opening 12b of the through cavity 12a of the flow rate adjusting nozzle 12 (hereinafter, referred to as projected parts S01' and S02'). FIG. 4 illustrates levels of the classification efficiency obtained by adjusting shadow area ratios of the projected parts S01' and S02'. As illustrated in FIG. 2, this embodiment uses five particle classifying sheets 14-1 to 14-5.

In FIG. 3A, the area ratio of the projected part S01, which is a shadowed part, is adjusted to a largest area ratio on the projection view formed by the whole five particle classifying sheets 14-1 to 14-5. Then, the area ratio of the projected part S01' facing the downstream-side opening 12b of the through cavity 12a provided in the flow rate adjusting nozzle 12 is accordingly adjusted to a largest area ratio.

The shadow area ratio is conventionally increased by slightly changing directions where the five particle classifying sheets 14-1 to 14-5 are disposed so that the mesh portions 14b do not overlap with one another at all or overlapping parts thereof, if any, are minimized. Substantially, a proportional relation exists between the area of the projected part S01 and the area of the projected part S01'.

In place of adjusting the area ratio of the projected part S0 to a largest area ratio on the projection view formed by the whole five particle classifying sheets 14-1 to 14-5, the area ratio of the projected part S01' in the range marked with a broken line that faces the downstream-side opening 12b of the through cavity 12a provided in the flow rate adjusting nozzle 12 may be directly adjusted to a largest area ratio. The adjustment of the area ratio to a smallest area ratio, which will be described later, is similarly performed.

Assuming that the whole area of the projection view is 100% in FIG. 3A, the area ratio of the projected part S01 to the whole area is 0.84 (=84%). In that case, the area ratio of the projected part S01" proportional to the projected part S01 in the range marked with a broken line is also 0.84 (=84%).

In FIG. 3B, the area ratio of the projected part S02, which is a shadowed part, is adjusted to a smallest area ratio on the projection view formed by the whole five particle classifying sheets 14-1 to 14-5. Then, the area ratio of the projected part S02' facing the downstream-side opening 12b of the through cavity 12a provided in the flow rate adjusting nozzle 12 is accordingly adjusted to a smallest area ratio.

The shadow area ratio is conventionally decreased by disposing the five particle classifying sheets 14-1 to 14-5 in almost the same direction or in exactly the same direction so that all of the mesh portions 14b overlap with one another or as many parts thereof as possible overlap with one another. Substantially, a proportional relation exits between the area of the projected part S02 and the area of the projected part S02'.

In FIG. 3B, the area ratio of the projected part S02 to the whole area of the projection view is 0.32 (=32%). In that case, the area ratio of the projected part S02' proportional to the projected part S02 in the range marked with a broken line is also 0.32 (=32%).

To simplify the description, the shadow area ratio on the projection view is adjusted in two different degrees; a largest area ratio (projected part S01), and a smallest area ratio (projected part S02). However, the shadow area ratio may be adjusted in more than two degrees.

FIG. 4 illustrates levels of the collection efficiency with different particle sizes and different shadow area ratios. In graph A, levels of the collection efficiency of the inertial filter in the projected part S01' of FIG. 3A (shadow area ratio 0.84 (=84%)) were measured and plotted. In graph B, levels of the collection efficiency of the inertial filter in the projected part S02' of FIG. 3B (shadow area ratio 0.32 (=32%)) were measured and plotted.

Figure 5:
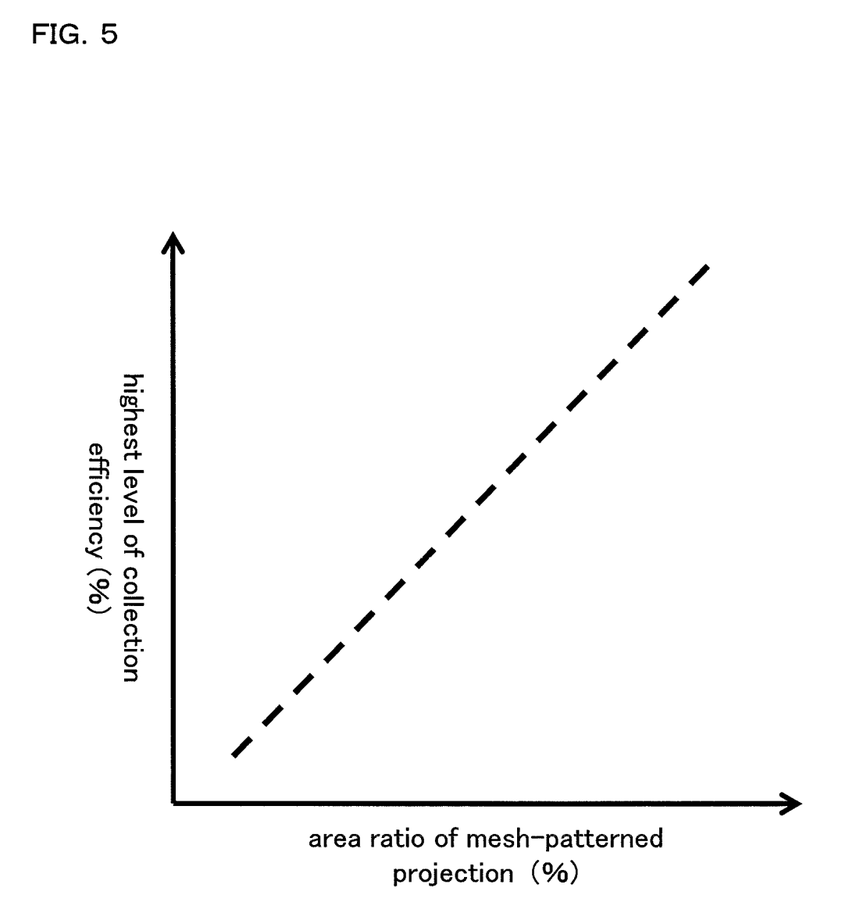

Comparing the graph A and B, the graph A shows the collection efficiency of 41% with the particle diameter 100 nm, and the graph shows the collection efficiency of 16% with the same particle size. Clearly, the collection efficiency impro FIG. 5 is a graph where the lateral axis represents the shadow area ratio ("area ratio of mesh-patterned projection" in the drawing) and the longitudinal axis represents a highest level of collection efficiency. It is known from FIG. 5 that the area ratio and the highest collection efficiency are in direct proportion to each other as illustrated with a dotted line. This teaches the significance of increasing the shadow area ratio in order to improve the collection efficiency.

Figure 6:
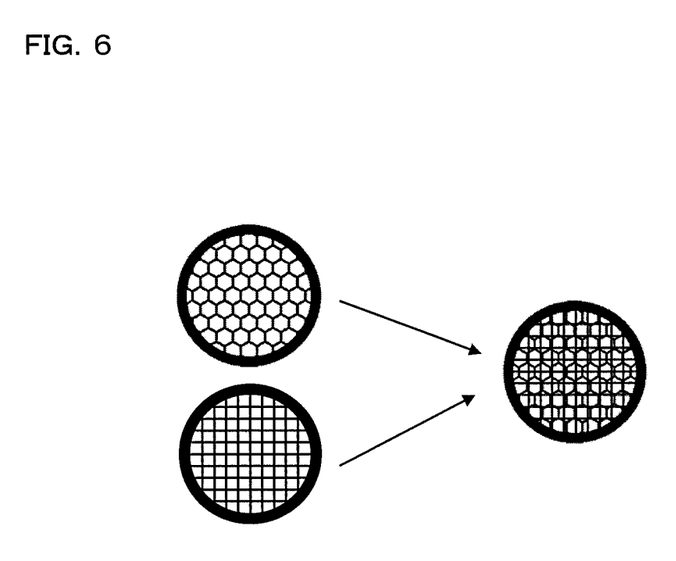

In the described example wherein the mesh-like holes are all square holes with exactly the same shape and dimensions, it is not possible to control the shadow area ratio if the particle classifying sheets are randomly combined. To deal with this, particle classifying sheets having asymmetric holes may be combined, in which case the shadow area ratio is controllable by the particle classifying sheets randomly combined. For example, a particle classifying sheet having square mesh-like holes and a particle classifying sheet having hexagonal mesh-like holes may be combined as illustrated in FIG. 6.

The particle classifying sheet having mesh-like holes is, for example, textiles woven with plastic fiber. Specific examples of the plastic fiber textiles are nylon mesh, polyester mesh, polypropylene mesh, Teflon (registered trademark) mesh, and polyethylene mesh. Further, textiles in which two or more different fibers are woven may be used, such as nylon mesh containing carbon fiber. As for metal fibers, SUS-woven mesh filters, or metallic films having a large number of minute through holes formed therein by etching, for example, may be used.

Figure 7:
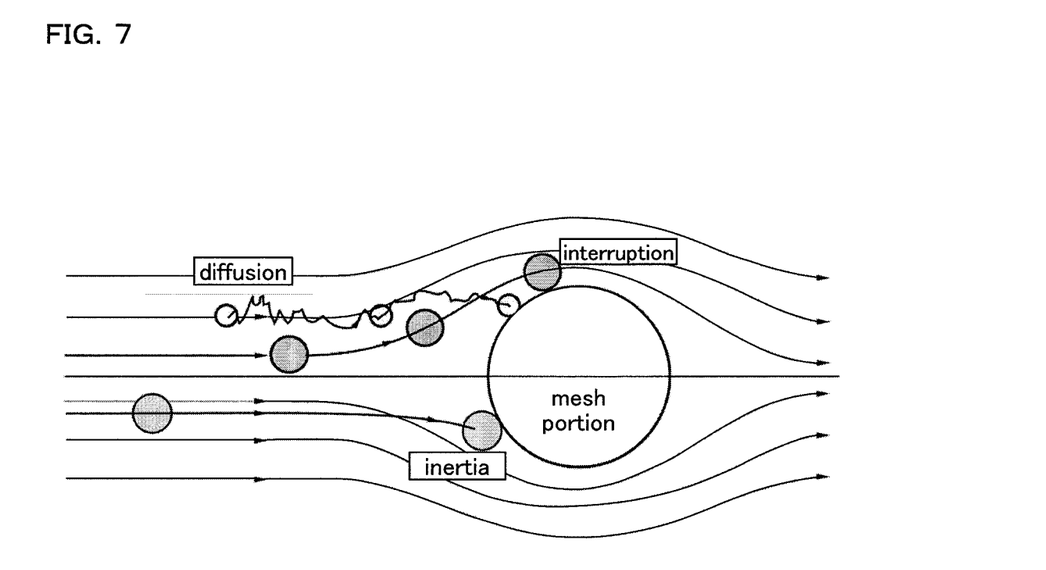

The particle collection mechanism and characteristics of the inertial filter 10 according to the embodiment are further described below. Referring to FIG. 7, a mechanism for collecting aerosol particles by using a conventional filter containing fiber layers (hereinafter, referred to as fiber-layered filer) is described. FIG. 7 is a conceptual view illustrated to describe the particle collection mechanism when the conventional fiber-layered filter is used. In the drawing, a direction where the stream of air is passing is illustrated with arrows. At the center of the drawing is illustrated a sectional view of an incompressible fiber constituting the fiber-layered filter. There is a stream of aerosol particles having variously different particle sizes around the fiber. When the aerosol particles are collected by such a conventional fiber-layered filter, diffusion, inertia, and interruption respectively function as collection mechanisms, and the collection efficiency of each mechanism relies upon the particle sizes and filtering speed. The inertia functions as a more dominant collection mechanism as the particle sizes are larger and the filter speed is higher. The scale of inertia collection is a Stokes number defined by the following expression (1) The Brownian diffusion functions as a more dominant collection mechanism as the particle sizes are smaller and the filtering speed is lower. The scale of diffusion collection is a Peclet number defined by the following expression (2). The inertia functions as a more dominant collection mechanism as the Stokes number is larger, while the Brownian diffusion functions as a more dominant collection mechanism as the Peclet number is smaller. This drawing teaches the technical concept that the particles are collected by a mechanism different to "sifting".

[Expression 1]

$$Stk = \frac{C_c \rho_p d_p^2 u_0}{9 \mu d_f} \quad (1)$$

[Expression 2]

$$Pe = \frac{u_0 d_f}{D} \quad (2)$$

Figure 8:
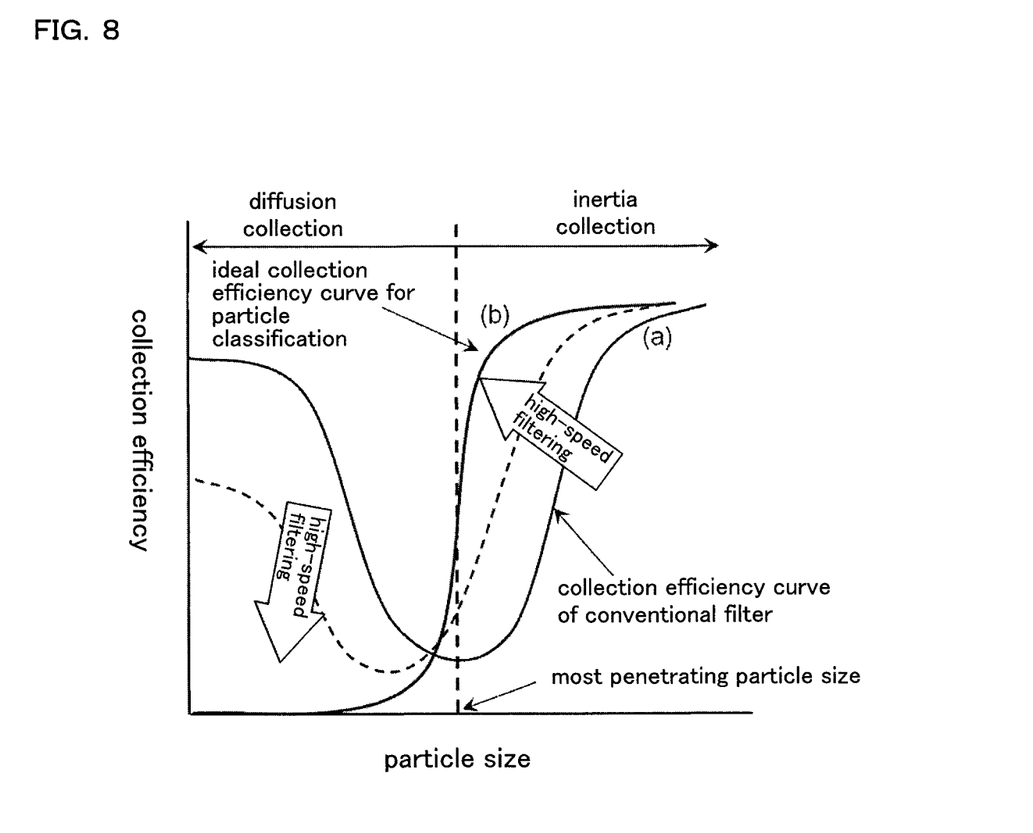

$C_c$ Cunningham slip correction factor
$d_p$: particle size (aerodynamic diameter)
$d_f$: diameter of collection fiber
D: diffusion coefficient of particle
$\rho^p$: density of particles
$u_0$: filtering speed
$\mu$: viscosity of fluid Plotting the collection efficiency of a conventional fine particle filter relative to the particle diameters, a curved line protruding downward illustrated in FIG. 8 (a) is obtained. There are the particle sizes that are most difficult to capture (poor collection efficiency), generally called "most penetrating particle size". The inertia functions as a more dominant collection mechanism with the most penetrating particle size and larger particle sizes, improving the collection efficiency with larger particle sizes.

On the other hand, the diffusion functions as a more dominant collection mechanism with the most penetrating particle size and smaller particle sizes, improving the collection efficiency with smaller particle sizes. When the filtering speed $u_0$ is increased, the Stokes number and the Peclet number defined by the expressions (1) and (2) accordingly increase. This strengthens the inertia collection but weakens the diffusion collection with small particle sizes. The curve illustrating the collection efficiency drawn in (a) changes into a curve illustrated with a dotted line as the filtering speed increases. When the filtering speed further increases, such a curve as illustrated in FIG. 8 (b) is drawn; a sharp rise in the collection efficiency with large particle sizes but a sharp drop in the collection efficiency with small particle sizes. The filter, wherein the aerosol particles are filtered by strengthening the inertia collection while weakening the diffusion collection as the filtering speed is higher, is called an inertial filter. The inertial filter ideally accomplishes the collection efficiency illustrated in the graph (b).

However, the kinetic energy of particles increases as the particle sizes are larger than submicron sizes. Then, the particles collided with the collection fibers by inertia may be accordingly bounced around and hard to capture.

Figure 9:
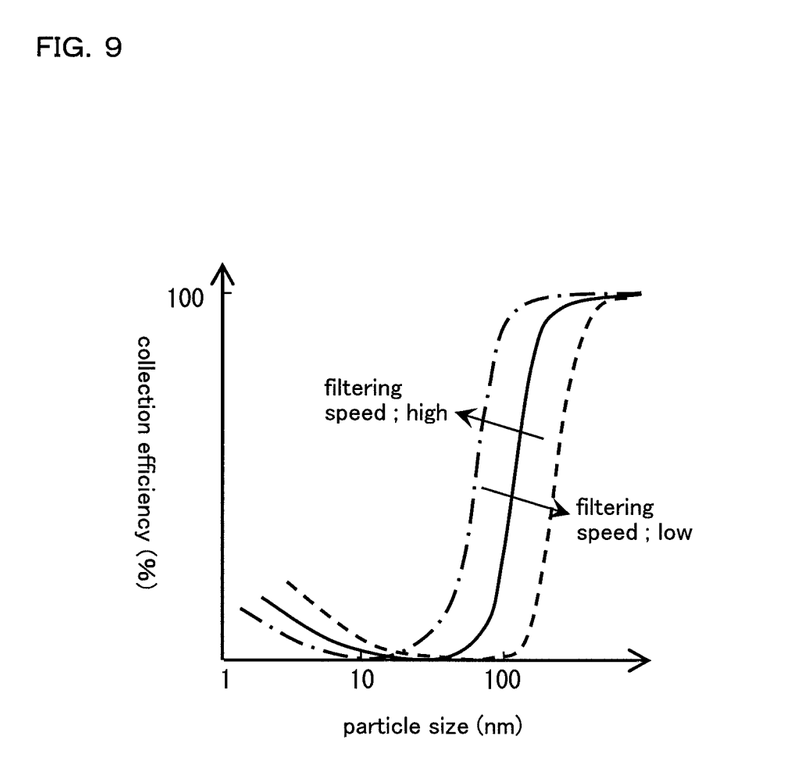

As described so far, the inertial filter is a low pass filter that strengthens the inertia collection while at the same time weakening the diffusion collection to collect submicron or smaller fine particles by filtering the aerosol particle at high speeds. This low pass filter can completely collect almost all of the particles having certain particle sizes or larger, while letting most of the other particles pass therethrough. Such a filter can be used as a classifier desirable for the classification of nanoparticles. As illustrated in FIG. 9, the inertial filter is characterized in that particles having smaller particle sizes are collected at higher filtering speeds. The inertial filet 10 can perform the inertial classification of nanoparticles by letting a stream of air pass through the mesh-like holes 14a of the particle classifying sheets 14-1 to 14-5 at relatively high speeds (several tens of m/sec).

Figure 10:
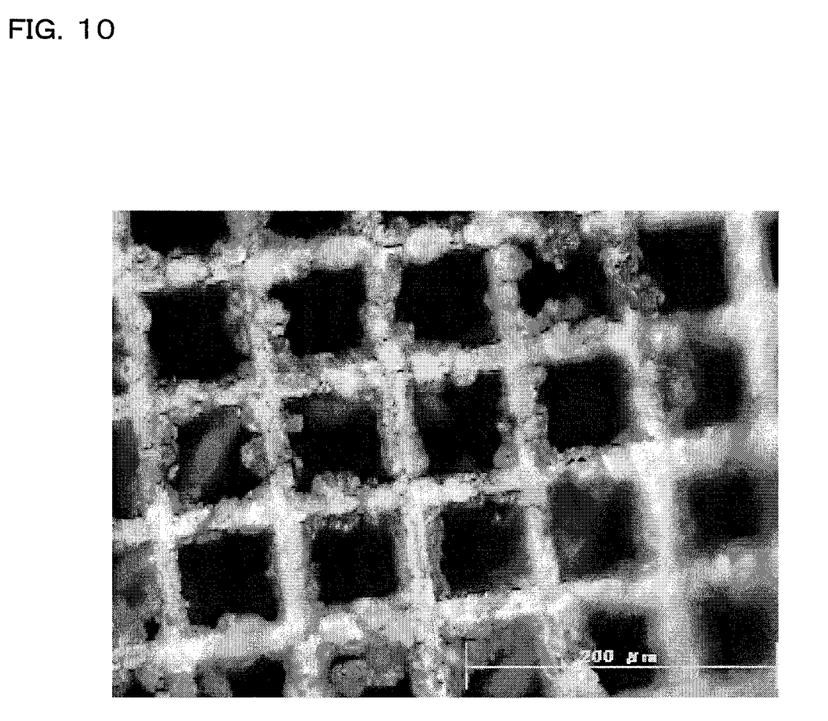

The photograph of FIG. 10 shows a state where particles are captured by and accumulated on a mesh-like filtering surface of the inertial filter illustrated in FIG. 2. The mesh specification of the particle classifying sheet provided in the inertial filter of the photograph is, fiber diameter: 10 μm, pitch: 80 μm, and aperture: 73 μm. It is known from the photograph that fine particles having particle sizes smaller than the mesh aperture are captured by and accumulated on the mesh-like filtering surface, which demonstrates the conceptual views of FIGS. 7 and 8.

The invention claimed is:

1. An inertial filter to be disposed in an air flow path for a stream of air containing nanoparticles having particle sizes equal to or smaller than 100 nm to pass through, the inertial filter being configured to collect the nanoparticles in the air flow path by utilizing an effect of particle inertia, the inertial filter collecting configured to collect the nanoparticles having smaller particle sizes as a flow velocity of the stream of air increases, the inertial filter comprising: a plurality of flow adjusting nozzles each having a different number of through cavities or having a through cavity diametrically reduced by a different diameter ratio, one of the flow quantity adjusting nozzles being located on an upstream side of the air flow path containing nanoparticles having particle sizes equal to or smaller than 100 nm; and
- a plurality of particle classifying sheets stacked and located on each other in a manner that the plurality of particle classifying sheets seal a whole surface of a downstream-side opening of the through cavity of the flow quantity adjusting nozzle;
- wherein each of the flow quantity adjusting nozzles is configured to be replaceable with another of the flow quantity adjusting nozzles having a different number of through cavities or having a through cavity diametrically reduced by a different diameter reducing ratio to allow for adjustment of the flow velocity, thereby strengthening inertia collection while weakening diffusion collection; and
- wherein the plurality of particle classifying sheets comprises a plurality of holes and mesh portions defining the plurality of holes so that the plurality of holes constitute meshes whose mesh aperture is larger than the particle size of the nanoparticles in order to classify the nanoparticles; and
- wherein the plurality of particle classifying sheets are configured to adjust a shadow area ratio on of a projected part relative to whole area of a projection view obtained by virtually projecting the plurality of particle classifying sheets from a downstream side to an upstream side of the air flow path to a value greater than 0.32 to thereby increase collection efficiency of the nanoparticle at the projected part.

2. The inertial filter as claimed in claim 1, wherein the plurality of particle classifying sheets are stacked on each other with a spacer interposed therebetween.

3. The inertial filter as claimed in claim 1,
- wherein the plurality of particle classifying sheets comprises an adjustable classification diameter which is an effective classification diameter of the inertial filter that is defined as a size of a shadow area ratio of a projection view obtained by virtually projecting the plurality of particle classifying sheets from a downstream side to an upstream side of the air flow path; and
- wherein the effective classification diameter is adjustable by altering relative transverse position of one or more of the plurality of particle classifying sheets; and
- wherein the effective classification diameter is adjustable to decrease size of nanoparticles collected by increasing said flow velocity.

* * * * *